United States Patent
Thompson et al.

(10) Patent No.: US 10,529,044 B2
(45) Date of Patent: Jan. 7, 2020

(54) TRACKING AND DELIVERY CONFIRMATION OF PHARMACEUTICAL PRODUCTS

(75) Inventors: Todd Thompson, San Jose, CA (US); Lawrence Arne, Palo Alto, CA (US); Fataneh Omidvar, Danville, CA (US); Yashar Behzadi, San Francisco, CA (US); Robert Duck, San Francisco, CA (US); Lorenzo Dicarlo, San Francisco, CA (US); Gregory Moon, Palo Alto, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 13/698,953

(22) PCT Filed: May 19, 2011

(86) PCT No.: PCT/US2011/037236
§ 371 (c)(1),
(2), (4) Date: Nov. 19, 2012

(87) PCT Pub. No.: WO2011/146767
PCT Pub. Date: Nov. 24, 2011

(65) Prior Publication Data
US 2013/0073312 A1    Mar. 21, 2013

Related U.S. Application Data

(60) Provisional application No. 61/346,035, filed on May 19, 2010.

(51) Int. Cl.
*G06F 19/00* (2018.01)
*G06Q 50/22* (2018.01)
(Continued)

(52) U.S. Cl.
CPC ............... *G06Q 50/22* (2013.01); *A61M 3/00* (2013.01); *G06F 19/3462* (2013.01);
(Continued)

(58) Field of Classification Search
CPC ........ A61M 2205/6054; G06F 19/3462; G06F 19/327; G06F 19/3443; G06F 19/3456;
(Continued)

(56) References Cited

U.S. PATENT DOCUMENTS 3,218,638 A  11/1965  Honig
3,345,989 A  10/1967  Reynolds
(Continued)

FOREIGN PATENT DOCUMENTS

CA    2953847    11/2006
CN    1588649    3/2005
(Continued)

OTHER PUBLICATIONS

Hotz "The Really Smart Phone" The Wall Street Journal, What They Know (2011); 6 pp.; http://online.wsj.com/article/SB10001424052748704547604576263261679848814.html?mod=djemTECH_t.
(Continued)

*Primary Examiner* — Hiep V Nguyen
(74) *Attorney, Agent, or Firm* — K&L Gates LLP

(57) ABSTRACT

A system and method are disclosed that track a deliverable to a user. The system includes an identifier or tag secured to the deliverable, a computer system for interrogating the identifier, and a personal device in communication with the computer system, wherein the personal device is held by the user at the time the user is administered the deliverable to detect the unique identity associated with the identifier device and confirms delivery of the deliverable to the user. The method includes attaching an identifiable tag that pro-
(Continued)

duces a unique signature to the deliverable, interrogating the tag at about the time of delivery to the user, and confirming that the user has been administered the deliverable through detecting the identifiable tag.

23 Claims, 3 Drawing Sheets

(51) Int. Cl.
  *A61M 3/00* (2006.01)
  *G08C 15/06* (2006.01)
  *H04N 7/18* (2006.01)
(52) U.S. Cl.
  CPC ............... *G08C 15/06* (2013.01); *H04N 7/18* (2013.01); *G06F 19/3468* (2013.01)
(58) Field of Classification Search
  CPC .......... G06F 19/3468; G06K 2017/009; G07F 17/0092; G07F 11/002; G06Q 10/087; G06Q 10/06; G06Q 10/08; G07G 1/0045; G07G 1/009; A61J 7/0084; A61J 2205/30; A61J 2205/60
  USPC .......................................................... 705/2
  See application file for complete search history.

(56) References Cited

U.S. PATENT DOCUMENTS

| | | |
|---|---|---|
| 3,353,539 A | 11/1967 | Preston |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| D377,983 S | 2/1987 | Sabri et al. |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,538,007 A | 7/1996 | Gorman |
| 5,551,953 A * | 9/1996 | Lattin .............. A61B 5/14514 600/582 |
| 5,567,210 A | 10/1996 | Bates et al. |
| 5,596,302 A | 1/1997 | Mastrocola et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,701 A | 6/1999 | Gersheneld et al. |
| 5,917,346 A | 6/1999 | Gord |
| 5,921,925 A | 7/1999 | Cartmell et al. |
| 5,925,030 A | 7/1999 | Gross et al. |

(56) References Cited

U.S. PATENT DOCUMENTS

| | | |
|---|---|---|
| 5,925,066 A | 7/1999 | Kroll et al. |
| 5,957,854 A | 9/1999 | Besson et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 3/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,069,062 B2 | 6/2006 | Minotani et al. |
| 7,076,437 B1 | 7/2006 | Levy |
| 7,081,693 B2 | 7/2006 | Hamel et al. |
| 7,091,726 B2 | 8/2006 | Sano et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |

(56) References Cited

U.S. PATENT DOCUMENTS

| | | |
|---|---|---|
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,014 B2 | 11/2007 | Chung et al. |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,449,262 B2 | 11/2008 | Christie et al. |
| 7,462,150 B1 | 12/2008 | Bharmi |
| 7,471,665 B2 | 12/2008 | Perlman |
| 7,485,093 B2 | 2/2009 | Glukhovsky |
| 7,485,095 B2 | 2/2009 | Shusterman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,558,622 B2 | 7/2009 | Tran |
| 7,558,965 B2 | 7/2009 | Wheeler et al. |
| 7,575,005 B2 | 8/2009 | Mumford |
| 7,614,743 B2 | 11/2009 | Geiger |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,683,761 B2 | 2/2010 | Burghard et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,764,996 B2 | 7/2010 | Zhang et al. |
| 7,779,614 B1 | 8/2010 | McGonagle et al. |
| 7,797,033 B2 | 9/2010 | D'Andrea et al. |
| 7,806,852 B1 * | 10/2010 | Jurson ............................ 604/65 |
| 7,809,399 B2 | 10/2010 | Lu |
| 7,811,231 B2 | 10/2010 | Jin et al. |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,871,734 B2 | 1/2011 | Hertz et al. |
| 7,899,526 B2 | 3/2011 | Benditt et al. |
| 7,904,133 B2 | 3/2011 | Gehman et al. |
| D639,437 S | 6/2011 | Bishay et al. |
| 8,036,731 B2 | 10/2011 | Kimchy et al. |
| 8,036,748 B2 | 10/2011 | Zdeblick et al. |
| 8,060,249 B2 | 11/2011 | Bear et al. |
| 8,073,707 B2 | 12/2011 | Teller et al. |
| 8,083,128 B2 | 12/2011 | Dembo et al. |
| 8,123,576 B2 | 2/2012 | Kim |
| 8,135,596 B2 | 3/2012 | Jung et al. |
| 8,142,513 B2 | 3/2012 | Shalon et al. |
| 8,177,611 B2 | 5/2012 | Kang |
| 8,180,425 B2 | 5/2012 | Selvitelli et al. |
| 8,185,191 B1 | 5/2012 | Shapiro et al. |
| 8,185,646 B2 | 5/2012 | Headley |
| 8,200,320 B2 | 6/2012 | Kovacs |
| 8,209,018 B2 | 6/2012 | Osorio et al. |
| 8,214,007 B2 | 7/2012 | Baker et al. |
| 8,224,667 B2 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2 | 8/2012 | Rofougaran |
| 8,258,962 B2 | 9/2012 | Robertson et al. |
| 8,262,394 B2 | 9/2012 | Walker et al. |
| 8,285,356 B2 | 10/2012 | Bly et al. |

(56) References Cited

U.S. PATENT DOCUMENTS

| | | |
|---|---|---|
| 8,290,574 B2 | 10/2012 | Felid et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,440,274 B2 | 5/2013 | Wang |
| 8,454,528 B2 | 6/2013 | Yuen et al. |
| 8,514,086 B2 | 8/2013 | Harper et al. |
| 8,542,123 B2 | 9/2013 | Robertson |
| 8,545,402 B2 | 10/2013 | Hafezi et al. |
| 8,564,432 B2 | 10/2013 | Covannon et al. |
| 8,564,627 B2 | 10/2013 | Suzuki et al. |
| 8,583,227 B2 | 11/2013 | Savage et al. |
| 8,597,186 B2 | 12/2013 | Hafezi et al. |
| 8,634,838 B2 | 1/2014 | Hellwig et al. |
| 8,660,645 B2 | 2/2014 | Stevenson et al. |
| 8,668,643 B2 | 3/2014 | Kinast |
| 8,668,645 B2 | 3/2014 | Heller et al. |
| 8,718,193 B2 | 5/2014 | Arne et al. |
| 8,722,085 B2 | 5/2014 | McKinney et al. |
| 8,771,183 B2 | 7/2014 | Sloan |
| 8,810,260 B1 | 8/2014 | Zhou |
| 8,810,409 B2 | 8/2014 | Robertson et al. |
| 8,823,510 B2 | 9/2014 | Downey et al. |
| 8,836,513 B2 | 9/2014 | Hafezi et al. |
| 8,838,217 B2 | 9/2014 | Myr |
| 8,868,453 B2 | 10/2014 | Zdeblick |
| 8,908,943 B2 | 12/2014 | Berry et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,956,287 B2 | 2/2015 | Zdeblick et al. |
| 8,956,288 B2 | 2/2015 | Hafezi et al. |
| 8,966,973 B1 | 3/2015 | Milone |
| 8,989,837 B2 | 3/2015 | Weinstein et al. |
| 9,031,658 B2 | 5/2015 | Chiao et al. |
| 9,047,746 B1 | 6/2015 | Euliano et al. |
| 9,088,168 B2 | 7/2015 | Mach et al. |
| 9,119,918 B2 | 9/2015 | Robertson et al. |
| 9,125,868 B2 | 9/2015 | McKinney et al. |
| 9,189,941 B2 | 11/2015 | Eschelman et al. |
| 9,226,663 B2 | 1/2016 | Fei |
| 9,226,679 B2 | 1/2016 | Balda |
| 9,235,683 B2 | 1/2016 | Robertson et al. |
| 9,258,035 B2 | 2/2016 | Robertson et al. |
| 9,270,025 B2 | 2/2016 | Robertson et al. |
| 9,277,864 B2 | 3/2016 | Yang et al. |
| 9,278,177 B2 | 3/2016 | Edwards et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,444,503 B2 | 9/2016 | Arne et al. |
| 9,517,012 B2 | 12/2016 | Lane et al. |
| 9,603,550 B2 | 3/2017 | Behzadi |
| 9,883,819 B2 | 2/2018 | Jensen et al. |
| 2001/0027331 A1 | 10/2001 | Thompson |
| 2001/0031071 A1 | 10/2001 | Nichols et al. |
| 2001/0039503 A1 | 11/2001 | Chan et al. |
| 2001/0044588 A1 | 11/2001 | Mault |
| 2001/0051766 A1 | 12/2001 | Gazdinski |
| 2001/0056262 A1 | 12/2001 | Cabiri et al. |
| 2002/0002326 A1 | 1/2002 | Causey et al. |
| 2002/0019586 A1 | 2/2002 | Teller et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0067270 A1 | 6/2002 | Yarin et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0138009 A1 | 9/2002 | Brockway et al. |
| 2002/0184415 A1 | 12/2002 | Naghavi et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0037063 A1 | 2/2003 | Schwartz |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1* | 9/2003 | Andreasson et al. ......... 235/385 |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0198619 A1 | 10/2003 | Dong et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0216793 A1 | 11/2003 | Karlsson et al. |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukuda et al. |
| 2004/0121015 A1 | 6/2004 | Chidlaw et al. |
| 2004/0122296 A1 | 6/2004 | Hatlestad |
| 2004/0122297 A1 | 6/2004 | Stahmann et al. |
| 2004/0138558 A1 | 7/2004 | Dunki-Jacobs et al. |
| 2004/0147326 A1 | 7/2004 | Stiles |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |

(56) References Cited

U.S. PATENT DOCUMENTS

| | | |
|---|---|---|
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |
| 2005/0038321 A1 | 2/2005 | Fujita et al. |
| 2005/0038680 A1 | 2/2005 | McMahon |
| 2005/0043583 A1 | 2/2005 | Killman et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0204764 A1 | 9/2006 | Hirao et al. |
| 2006/0210626 A1* | 9/2006 | Spaeder .................... 424/464 |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0172424 A1 | 7/2007 | Roser |
| 2007/0173701 A1 | 7/2007 | Al-Ali |
| 2007/0177770 A1* | 8/2007 | Derchak ............ G06K 9/00496 382/115 |
| 2007/0179347 A1 | 8/2007 | Tarassenko et al. |
| 2007/0179371 A1 | 8/2007 | Peyser et al. |
| 2007/0180047 A1 | 8/2007 | Dong et al. |

(56) References Cited

U.S. PATENT DOCUMENTS

| | | |
|---|---|---|
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 * | 2/2008 | DellaVecchia et al. ...... 600/477 |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 * | 1/2009 | Weinert et al. ............... 705/3 |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |

(56) References Cited

U.S. PATENT DOCUMENTS

| | | |
|---|---|---|
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1 | 4/2010 | Zdeblick et al. |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1* | 7/2010 | Smith .................. G06F 19/322 |
| | | 382/117 |
| 2010/0185055 A1 | 7/2010 | Robertson |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1 | 1/2011 | O'Reilly et al. |
| 2011/0021983 A1* | 1/2011 | Jurson .................. A61B 5/1172 |
| | | 604/93.01 |
| 2011/0029622 A1 | 2/2011 | Walker et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |

(56) References Cited

U.S. PATENT DOCUMENTS

| | | | |
|---|---|---|---|
| 2012/0011699 A1 | 1/2012 | Hafezi et al. |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelsen et al. |
| 2012/0265544 A1 | 10/2012 | Hwang et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0171596 A1 | 7/2013 | French |
| 2013/0185228 A1 | 7/2013 | Dresner |
| 2013/0196012 A1 | 8/2013 | Dill |
| 2013/0275296 A1 | 10/2013 | Tietzen et al. |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0203950 A1 | 7/2014 | Zdeblick et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0334575 A1 | 11/2014 | Arne et al. |
| 2014/0349256 A1 | 11/2014 | Connor |
| 2014/0374276 A1 | 12/2014 | Guthrie et al. |
| 2015/0048929 A1 | 2/2015 | Robertson et al. |
| 2015/0051465 A1 | 2/2015 | Robertson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0165313 A1 | 6/2015 | Thompson et al. |
| 2015/0171924 A1 | 6/2015 | Zdeblick |
| 2015/0182463 A1 | 7/2015 | Hafezi et al. |
| 2015/0193593 A1 | 7/2015 | Zdeblick et al. |
| 2015/0230728 A1 | 8/2015 | Hafezi et al. |
| 2016/0106339 A1 | 4/2016 | Behzadi et al. |
| 2016/0155316 A1 | 6/2016 | Hafezi et al. |
| 2017/0000180 A1 | 1/2017 | Arne et al. |
| 2017/0215761 A1 | 8/2017 | Zdeblick |
| 2017/0270779 A1 | 9/2017 | Zdeblick et al. |
| 2017/0290513 A1 | 10/2017 | O'Reilly et al. |
| 2017/0303818 A1 | 10/2017 | Behzadi et al. |
| 2018/0026680 A1 | 1/2018 | Shirvani et al. |
| 2018/0184698 A1 | 7/2018 | Arne et al. |
| 2018/0279910 A1 | 10/2018 | Jensen et al. |

FOREIGN PATENT DOCUMENTS

| | | |
|---|---|---|
| CN | 2748032 | 12/2005 |
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 2143369 | 1/2010 |
| GB | 775071 | 5/1957 |
| GB | 2432862 | 6/2007 |
| IL | 172917 | 6/2010 |
| JP | 61017949 | 1/1986 |
| JP | S63280393 | 11/1988 |
| JP | H01285247 | 11/1989 |
| JP | 05-228128 | 9/1993 |
| JP | H0646539 | 2/1994 |
| JP | H0884779 | 4/1996 |
| JP | 09-330159 | 12/1997 |
| JP | 10-14898 | 1/1998 |
| JP | H11195415 | 7/1999 |
| JP | 2000-506410 | 5/2000 |
| JP | 2001078974 | 3/2001 |
| JP | 2002-224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 2003325440 | 11/2003 |
| JP | 2004-7187 | 1/2004 |
| JP | 2004507188 | 3/2004 |
| JP | 2004-134384 | 4/2004 |
| JP | 2004274452 | 9/2004 |
| JP | 2004-313242 | 11/2004 |
| JP | 2004318534 | 11/2004 |
| JP | 2004364016 | 12/2004 |
| JP | 2005031840 | 2/2005 |
| JP | 2005-073886 | 3/2005 |
| JP | 2005-087552 | 4/2005 |
| JP | 2005-304880 | 4/2005 |
| JP | 2005124708 | 5/2005 |
| JP | 2005148021 | 6/2005 |
| JP | 2005152037 | 6/2005 |
| JP | 2005287691 | 10/2005 |
| JP | 2005-532841 | 11/2005 |
| JP | 2005-532849 | 11/2005 |
| JP | 2005343515 | 12/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007200739 | 8/2007 |
| JP | 2007-313340 | 12/2007 |
| JP | 2007-330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |
| JP | 2009034345 | 2/2009 |
| JP | 2009-061236 | 3/2009 |
| JP | 2009050541 | 3/2009 |
| JP | 2009065726 | 3/2009 |
| JP | 2011015817 | 1/2011 |
| JP | 2011519583 | 7/2011 |
| KR | 20020015907 | 3/2002 |
| KR | 20020061744 | 7/2002 |
| KR | 200609977523 | 7/2006 |
| KR | 927471 | 11/2009 |
| KR | 20110137001 | 12/2011 |
| KR | 10-2012-09995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |

(56) References Cited

FOREIGN PATENT DOCUMENTS

| | | |
|---|---|---|
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | WO0235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006109072 | 10/2006 |
| WO | WO2006116718 | 11/2006 |
| WO | WO2006119345 | 11/2006 |
| WO | WO2006123346 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |

(56) References Cited

FOREIGN PATENT DOCUMENTS

| WO | WO2013012869 | 1/2013 |
|---|---|---|
| WO | WO2015112603 | 7/2015 |

OTHER PUBLICATIONS

Evanczuk, S., "PIC MCU software library uses human body for secure communications link" EDN Network; edn.com; Feb. 26, 2013 Retrieved from Internet Jun. 19, 2013 at http://www.edn.com/electronics-products/other/4407842/PIC-MCU-software-library-uses-human-body-for-secure-communications-link; 5 pp.

AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.

Arshak et al., A Review and Adaptation of Methods of Object Tracking to Telemetry Capsules IC-Med; Jan. 2007 vol. 1, No. 1, Issue 1, 12pp.

"ASGE Technology Status Evaluation Report: wireless capsule endoscopy" American Soc. For Gastrointestinal Endoscopy; Apr. 2006 vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; Sep. 2003; Abstract Only.

Barrie, Heidelberg pH capsule gastric analysis. Texbook of Natural Medicine, (1992), Pizzorno, Murray & Barrie.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastoenterology; Oct. 2008 vol. 22, Issue 5, 1pp. (Abstract Only).

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf.

Ferguson et al., "Dielectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget; Mar. 2012 http://medgadget.com/2012/03/put-your-phone-or-skin-on-vibrate.html 8pp.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng; Dec. 2007 54(12) 1pp. (Abstract Only).

Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.

Halthion Medical Technologies "Providing Ambulatory Medical Devices Which Monitor, Measure and Record" webpage. Online website: http://www.halthion.com/; downloaded May 30, 2012.

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider May 2010 http://www.e-health-insider.com/news/5910/new_'smartpill'_monitors_medicines.

Hoover et al., "Rx for health: Engineers design pill that signals it has been swallowed" University of Florida News; Mar. 2010 2pp.; http://news.ufl.edu/2010/03/31/antenna-pill-2/.

ISFET—Ion Sensitive Field-Effect Transistor; Microsens S.A. pdf document. First in Office Action dated Jun. 13, 2011 for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Jung, S. "Dissolvable 'Transient Electronics' Will be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Juvenile Diabetes Research Foundation International (JDRF), "Artificial Pancreas Project" Jun. 2010; http://www.artificialpancreasproject.com/; 3 pp.

Kamada K., "Electrophoretic deposition assisted by soluble anode" Materials Letters 57 (2003) 2348-2351.

Li, P-Y, et al. "An electrochemical intraocular drug delivery device", Sensors and Actuators A 143; p. 41-48.; Jul. 2007.

Lifescan, "OneTouch UltraLink™" http://www.lifescan.com/products/meters/ultralink; Jul. 2010 2 pp.

Lin et al., "Do Physiological Data Relate to Traditional Usability Indexes?" Proceedings of OZCHI 2005, Canberra, Australia (2005) 10 pp.

Mackay et al., "Radio Telemetering from within the Body Inside Information is Revealed by Tiny Transmitters that can be Swallowed or Implanted in Man or Animal" Science (1991) 1196-1202; 134; American Association for the Advancement of Science, Washington D.C.

Mackay et al., "Endoradiosonde" Nature, (1957) 1239-1240, 179 Nature Publishing Group.

Mandryk et al., "A physiological approach for continuously modeling user emotion in interactive play environments" Proceedings of Measuring Behavior (2008) (Maastrichtm The Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

Mckenzie et al., "Validation of a new telemetric core temperature monitor" J. Therm. Biol. (2004) 29(7-8):605-11.

Medtronic, "CareLink Therapy Management Software for Diabetes" Jul. 2010; https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® Real-Time Revel™ System" Aug. 2010 http://www.medtronicdiabetes.com/products/index.html; 2 pp.

Medtronic, "Mini Med Paradigm® Revel™ Insulin Pump" Jul. 2010 http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

(56) References Cited

OTHER PUBLICATIONS

Melanson, "Walkers swallow RFID pills for science" Engadget; Jul. 2008; http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. MiniMitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description. Jul. 2005.
Minimitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html.
"PALO Bluetooth Baseband" PALO Bluetooth Resource Center (2002) Retrieved from internet Dec. 12, 2012 at URL:http://palowireless.com/bluearticles/baseband.asp; first cited in Office Action dated Jan. 17, 2013 for EP08853901.0.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
"RFID "pill" monitors marchers" RFID News; Jul. 2008 http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. Aug. 2009.
"The SmartPill Wireless Motility Capsule" Smartpill, The Measure of GI Health; May 2010 http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/13pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.
U.S. Appl. No. 12/238,345, filed Sep. 25, 2008, Hooman et al., Non-Final Office Action dated Jun. 13, 2011 22pp.
Walkey, "MOSFET Structure and Processing"; 97.398* Physical Electronics Lecture 20; First in Office Action dated Jun. 13, 2011 for U.S. Appl. No. 12/238,345; 24 pp.
Watson, et al., "Determination of the relationship between the pH and conductivity of gastric juice" Physiol Meas. 17 (1996) pp. 21-27.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
Kim et al., "A Semi-Interpenetrating Network System for a Polymer Membrane"; Eur. Polym. J. vol. 33 No. 7; pp. 1009-1014 (1997).
Winter, J. et al. "The material properties of gelatin gels"; USA Ballistic Research Laboratories, Mar. 1975, p. 1-157.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Whipple, Fred L.; "Endoradiosonde," Nature, Jun. 1957, 1239-1240.
Au-Yeung, K., et al., "A Networked System for Self-Management of Drug Therapy and Wellness", Wireless Health '10, Oct. 5-7, 2010, San Diego, 9 pages.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Ferguson et al., "Wireless communication with implanted medical devices using the conductive properties of the body," Expert Rev Med Devices, Jul. 2011, 8(4): 427-433.
Greene, "Medicaid Efforts to Incentivize Healthy Behaviours", Center for Health Care Strategies, Inc., Resource Paper, Jul. 2007.
McDermott-Wells, P., "What is Bluetooth?", IEEE Potentials, IEEE, New York, NY, vol. 23, No. 5, Dec. 1, 2004, pp. 33-35.
Chan, Adrian D.C., et al.,; "Wavelet Distance Measure for Person Identification Using Electrocardiograms," IEEE Transactions on

(56) References Cited

OTHER PUBLICATIONS

Instrumentation and Measurement, IEEE Service Center, Piscataway, NJ, US, vol. 57, No. 2, Feb. 1, 2008, pp. 248-253.
Zhang, Y-T. et al., "Wireless Biomedical Sensing," Wiley Encyclopedia of Biomedical Engineering, 2006, pp. 1-9.
Aronson, J., "Meyer's Side Effects of Cardiovascular Drugs," Elsevier, Mar. 2, 2009, Medical, 840 pages. (Not Attached).
Herbig, S.M., "Asymmetric-membrane tablet coatings for osmotic drug delivery", Journal of Controlled Release 35 (1995) 127-136.
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Sammoura, F. et al., "Water-activated disposable and long shelf life microbatteries", Sensors and Actuators A 111 (2004) 79-86.
VonStetten, F. et al., "Biofuel cells as power generation for implantable devices", Pore. Eurosensors XX, (2006), pp. 22-225.
Van der Biest, O., et al., "Electrophoretic deposition of materials," Annu. Rev. Mater. Sci. 1999, 29: pp. 327-352.
Browne, S.H., et al., "Let visuals tell the story: Medication adherence in patients with type II diabetes captured by a novel ingestion sensor platform," JMIR Mhealth Uhealth; 3(4): e108; 2015; 27 pages.
Frias, J. et al., "Effectiveness of Digital Medicines to Improve Clinical Outcomes in Patients with Uncontrolled Hypertension and Type 2 Diabetes: Prospective, Open-Label, Cluster-Randomized Pilot Clinical Trial," J Med Internet Res, 2017;19(7):e246; p. 15 (16 pages).
Noble et al., "Medication adherence and activity patterns underlying uncontrolled hypertension: Assessment and recommendations by practicing pharmacists using digital health care," JAPHA; 56 (2016) pp. 310-315 (6 pages).
Savage, G., "Predictive Analytics: Advancing Precision and Population Medicine," Harvard Health Policy Review, 2015; vol. 14; Issue 2; 4 pages.

\* cited by examiner

TRACKING AND DELIVERY CONFIRMATION OF PHARMACEUTICAL PRODUCTS

CROSS REFERENCE To RELATED APPLICATIONS

The present application is a U.S. national phase application filed under 35 U.S.C. § 371 of International Patent Application No. PCT/US2011/037236, entitled "TRACKING AND DELIVERY CONFIRMATION OF PHARMACEUTICAL PRODUCTS," filed May 19, 2011, which application claims the benefit under 35 U.S.C. § 119 (e) of U.S. Provisional Patent Application No. 61/346,035 entitled "TRACKING AND DELIVERY CONFIRMATION OF PHARMACEUTICAL PRODUCTS" and filed on May 19, 2010, which applications are hereby incorporated by reference in their entireties.

FIELD OF THE INVENTION

The present invention is related to electronic systems for tracking products from manufacturer to consumer and, more specifically, to multiple devices including a mobile communication unit and an identifiable tag that is associated with a pharmaceutical product to confirm source of the dosage, the proper type and amount of dose, and delivery to the patient.

INTRODUCTION

In many instances there is a need for tracking pharmaceutical products from the manufacturer to the patient. In so doing, the provider or dispenser of the pharmaceutical products is able to confirm that the pharmaceutical products come from a reliable source and that the pharmaceutical products are not counterfeit. Additionally, in many remote areas, where access to medical facilities is limited, it is often the case wherein the provider is not able to read or understand information provided on the label. In such situations, the provider needs a simple and effective way to identify the patient and determine what medication should be delivered, especially when there are various medications from which to choose.

Thus, what is needed is a system and method that can track pharmaceutical products from the manufacturer along the supply chain to the patient as well as confirm actual delivery of the pharmaceutical products to the patient.

SUMMARY

The present disclosure includes a system for tracking pharmaceutical products from manufacturer to the patient. The present invention also includes systems for confirming delivery of the pharmaceutical products to the patient; the delivery confirmation includes systems and methods for confirming delivery of the right dose and the correct quantity. The present invention includes systems that include circuitry and components that can function within certain environments that include a conducting fluid. One example of such an environment is outside or inside a container that houses the conducting fluid, such as a sealed bag with a solution, which includes an IV bag. Another example is within the body of a living organism, such as an animal or a human. According to various aspects of the present invention, part of the system is ingestible or injectible and, hence, can be taken by or injected to or inhaled by the patient.

In one aspect, a computer system is provided to track a medication from manufacturer to a patient, to enable a care provider to determine the origin of the medication and to confirm that at least one of the right type and the right dosage of the medication was delivered to the patient. The computer system comprising: a processor operative to: receive a unique identity of an identifier device secured to a dosage of medication, wherein the identifier device comprises the unique identity that is associated with at least one of the manufacturer and the medication; receive information from a patient interface device in communication with the computer and the patient, wherein at the time the patient takes the medication, the patient interface device is operative to detect the unique identity associated with the identifier device and confirm delivery of the medication to the patient; and receive the detected unique identity associated with the identifier device detected via the patient interface device and the confirmation of delivery of the medication to the patient via the patient interface device; wherein the processor is operative to confirm the origin of the medication and the type of the medication based at least on the unique identity of the identifier device.

In another aspect of the computer system, the processor is operative to interrogate the identifier device.

In another aspect of the computer system, the identifier device comprises a tag provided with circuitry, wherein the tag is secured to the dosage of the medication, and wherein the processor is operative to read the unique identity from the tag.

In another aspect of the computer system, the tag is secured to a dosage of medication in the form of a pill.

In another aspect of the computer system, the tag is secured to a syringe configured for delivery of the dosage of medication, wherein the syringe comprises a safety component which is activated upon exposure to air.

In another aspect of the computer system, the syringe comprises a needle and wherein the needle comprises at least one contact point coupled to the tag.

In another aspect of the computer system, the processor is operative to communicate with a datacenter database to at least one of retrieve medical information about the patient and provide information related to the medication to be administered to the patient.

In another aspect of the computer system, the processor is operative to: communicate with at least one of a database or a processing system at the datacenter; transmit information to the processing system; receive information from the processing system, wherein the processing system is operative to access the information in the database of the data center and provide the information to the patient through the computer.

In another aspect of the computer system, the processor is operative to validate at least one of the type and dosage selected by the care provider prior to dispensing the medication to the patient.

In another aspect of the computer system, the processor is operative to communicate with an interrogation unit coupled to the identifier device, wherein the interrogation unit is operative to interrogate the identifier device secured to the medication and receive the unique identity of the identifier device to confirm the origin of the medication and the type of the medication, wherein the computer is operative to interrogate the interrogation unit and receive the unique identity of the identifier from the interrogation unit.

In another aspect of the computer system, the processor is operative to: communicate with a memory of the interrogation unit; and receive the unique identity of the identifier stored in the memory of the interrogation unit.

In another aspect of the computer system, the processor is operative to receive biometric parameters from the patient interface device, wherein the biometric parameters can identify the patient.

In another aspect of the computer system, the processor is operative to receive an image of the patient captured by a camera on the patient interface device.

In another aspect of the computer system, a display provides information associated with the patient, wherein the information comprises any of an image of the patient, medical history of the patient, and a next type and dose of medication to deliver to the patient.

In one aspect, a computer-implemented method is provided to track a medication from manufacturer to a patient, to enable a care provider to determine the origin of the medication and to confirm that at least one of the right type and the right dosage of medication was delivered to the patient, the computer comprising a processor. The method comprising: receiving by the processor a unique identity of the identifier device secured to a dosage of medication, wherein the identifier device comprises the unique identity that is associated with at least one of the manufacturer and the medication; receiving by the processor information from a patient interface device in communication with the computer and the patient, wherein at the time the patient takes the medication, the patient interface device is operative to detect the unique identity associated with the identifier device and confirm delivery of the medication to the patient; receiving by the processor the detected unique identity associated with the identifier device detected from the patient interface device and the confirmation of delivery of the medication to the patient from the patient interface device; and confirming the origin of the medication and the type of the medication based at least on the unique identity of the identifier device.

In another aspect, the computer-implemented method comprises interrogating by the processor the identifier device.

In another, the computer-implemented method comprises receiving by the processor the unique identity from a tag, wherein the identifier device comprises the tag provided with circuitry, wherein the tag is secured to the dosage of the medication, the method.

In another aspect, the computer-implemented method comprises receiving by the processor the unique identity from the tag, wherein the tag is secured to a dosage of medication in the form of a pill.

In another aspect, the computer-implemented method comprises receiving by the processor the unique identity from the tag, wherein the tag is secured to a syringe configured for delivery of the dosage of medication, wherein the syringe comprises a safety component which is activated upon exposure to air.

In another aspect, the computer-implemented method comprises receiving by the processor the unique identity from the tag, wherein the syringe comprises a needle, and wherein the needle comprises at least one contact point coupled to the tag.

In another aspect, the computer-implemented method comprises at least one of: retrieving by the processor medical information about the patient from a datacenter database; and providing by the processor information related to the medication to be administered to the patient.

In another aspect, the computer-implemented method comprises transmitting by the processor information to the processing system; receiving by the processor information from the processing system, wherein the processing system is operative to access the information in the database of the data center and provide the information to the patient through the computer.

In another aspect, the computer-implemented method comprises validating by the processor at least one of the type and dosage selected by the care provider prior to dispensing the medication to the patient.

In another aspect, the computer-implemented method comprises interrogating by the processor operative an interrogation unit coupled to the identifier device, wherein the interrogation unit is operative to interrogate the identifier device secured to a medication and receive the unique identity of the identifier device to confirm the origin of the medication and the type of the medication; and receiving by the computer the unique identity of the identifier from the interrogation unit.

In another aspect, the computer-implemented method comprises communicating by the processor with a memory of the interrogation unit; and receiving by the processor the unique identity of the identifier stored in the memory of the interrogation unit.

In another aspect, the computer-implemented method comprises receiving by the processor biometric parameters from the patient interface device, wherein the biometric parameters can identify the patient.

In another aspect, the computer-implemented method comprises receiving by the processor an image of the patient captured by a camera on the patient interface device. In another aspect, the computer-implemented method comprises displaying on a display coupled to the processor information associated with the patient, wherein the information comprises any of an image of the patient, medical history of the patient, and a next type and dose of medication to deliver to the patient.

In one aspect, an apparatus is provided. The apparatus comprising: at least one contact point configured to electrically engage an identifier device secured to a medication, wherein the identifier device comprises a unique identity that is associated with at least one of the manufacturer and the medication; an interrogation unit coupled to the at least one contact point, wherein the interrogation unit is operative to interrogate the identifier device to obtain the unique identity; and a communication module coupled to the interrogation unit, wherein the communication module is operative to transmit the unique identification.

In another aspect of the apparatus, the interrogation unit is operative to read the unique identity associated with the identifier device.

In another aspect, the communication module is operative to transmit the unique identity associated with the identifier device to a computer in communication with the communication module.

In another aspect of the apparatus, the apparatus comprises a memory coupled to the interrogation unit to store the unique identity associated with the identifier device.

In another aspect, the interrogation unit is operative to read the unique identity from a tag provided with circuitry, wherein the tag is secured to the dosage of the medication.

In another aspect of the apparatus, the interrogation unit is operative to read the unique identity from the tag, wherein the tag is secured to a dosage of medication in the form of a pill.

In another aspect of the apparatus, the interrogation unit is operative to read the unique identity from the tag, wherein the tag is secured to a syringe configured for delivery of the dosage of medication, wherein the syringe comprises a safety component which is activated upon exposure to air.

In another aspect of the apparatus, the interrogation unit is operative to read the unique identity from the tag, wherein the syringe comprises a needle and wherein the needle comprises at least one contact point coupled to the tag.

In one aspect, a method is provided. The method comprising: electrically engaging by an interrogation unit an identifier device secured to a medication with at least one contact point coupled to the interrogation unit, wherein the identifier device comprises a unique identity that is associated with at least one of the manufacturer and the medication; interrogating the identifier device for the unique identity; and transmitting the unique identification by a communication module coupled to the interrogation unit.

In another aspect, the method comprises reading by the interrogation unit the unique identity associated with the identifier device.

In another aspect, the method comprises transmitting by the communication module the unique identity associated with the identifier device to a computer in communication with the communication module.

In another aspect, the method comprises storing by the interrogation unit the unique identity associated with the identifier device in a memory, wherein the memory is coupled to the interrogation unit.

In another aspect, the method comprises receiving by the interrogation unit the unique identity from a tag, wherein the identifier device comprises the tag provided with circuitry, wherein the tag is secured to the dosage of the medication.

In another aspect, the method comprises receiving by the interrogation unit the unique identity from the tag, wherein the tag is secured to a syringe configured for delivery of the dosage of medication, wherein the syringe comprises a safety component which is activated upon exposure to air.

In another aspect, the method comprises receiving by the interrogation unit the unique identity from the tag, wherein the tag is secured to a syringe configured for delivery of the dosage of medication, wherein the syringe comprises a safety component which is activated upon exposure to air.

In another aspect, the method comprises receiving by the interrogation unit the unique identity from the tag, wherein the syringe comprises a needle, and wherein the needle comprises at least one contact point coupled to the tag.

In one aspect, a patient interface device is provided. The patient interface comprising: a housing defining an outer surface, wherein the housing is configured to held by a patient; at least one contact point exposed on the outer surface portion of the housing, wherein the at least one contact point is positioned to be physically contacted by the patient to detect biometric information associated with the patient, wherein the at least one contact point is configured to detect at least one physiological parameter associated with the patient; a control module coupled to the at least one contact point, wherein the at least one contact point is coupled to the control module to capture the at least one physiological parameter associated with the patient; and a communication module coupled to the control unit to transmit the at least one physiological parameter to a computer in communication with the communication module.

In another aspect of the patient interface device, the patient interface device comprises a power source coupled to the control module.

In another aspect of the patient interface device, the patient interface device comprises an image generation unit to capture an image of the patient, wherein the image generation unit is coupled to the control module and is configured to capture the image of the patient and to transmit the captured image to the control module.

In another aspect of the patient interface device, the control module is operative to activate the image generation unit to capture the image of the patient when the contact point detects there is a change in the physiological parameter of the patient during the time the patient is in contact with the contact point and when the control module detects a current flow through the patient.

In one aspect, a method is provided. The method comprising: contacting by a patient at least one contact point exposed on an outer surface portion of a housing, wherein the at least one contact point is positioned to be physically contacted by the patient to detect biometric information associated with the patient, wherein the at least one contact point is configured to detect at least one physiological parameter associated with the patient; capturing by a control module coupled to the at least one contact point at least one physiological parameter associated with the patient; and transmitting by a communication module coupled to the control unit the at least one physiological parameter to a computer in communication with the communication module.

In another aspect, the method comprises scanning by the at least contact point a fingerprint associated with the patient; confirming by the control module fingerprint information.

In another aspect, the method comprises capturing an image of the patient by an image generation unit, wherein the image generation unit is coupled to the control module; and transmitting by the image generation unit the captured image of the patient to the control module.

In another aspect, the method comprises activating by the control module the image generation unit to capture the image of the patient when the contact point detects there is a change in the physiological parameter of the patient during the time the patient is in contact with the contact point and when the control module detects a current flow through the patient.

In one aspect, a patient interface device is provided. The patient interface device comprising: a housing defining an outer surface, wherein the housing is configured to held by a patient; at least one contact point exposed on the outer surface portion of the housing, wherein the at least one contact point is positioned to be physically contacted by the patient to detect biometric information associated with the patient, wherein the at least one contact point is configured to detect at least one physiological parameter associated with the patient; a control module coupled to the at least one contact point, wherein the at least one contact point is coupled to the control module to capture the at least one physiological parameter associated with the patient; and a communication module coupled to the control unit to transmit the at least one physiological parameter to a computer in communication with the communication module.

In another aspect, the patient interface device comprises a power source coupled to the control module.

In another aspect, the patient interface device comprises an image generation unit to capture an image of the patient, wherein the image generation unit is coupled to the control module and is configured to capture the image of the patient and to transmit the captured image to the control module.

In another aspect of the patient interface device, the control module is operative to activate the image generation unit to capture the image of the patient when the contact point detects there is a change in the physiological parameter of the patient during the time the patient is in contact with the contact point and when the control module detects a current flow through the patient.

In one aspect, a method is provided. The method comprising: contacting by a patient at least one contact point exposed on an outer surface portion of a housing, wherein the at least one contact point is positioned to be physically contacted by the patient to detect biometric information associated with the patient, wherein the at least one contact point is configured to detect at least one physiological parameter associated with the patient; capturing by a control module coupled to the at least one contact point at least one physiological parameter associated with the patient; and transmitting by a communication module coupled to the control unit the at least one physiological parameter to a computer in communication with the communication module.

In another aspect, the method comprises scanning by the at least contact point a fingerprint associated with the patient; confirming by the control module fingerprint information.

In another aspect, the method comprises capturing an image of the patient by an image generation unit, wherein the image generation unit is coupled to the control module; and transmitting by the image generation unit the captured image of the patient to the control module.

In another aspect, the method comprises activating by the control module the image generation unit to capture the image of the patient when the contact point detects there is a change in the physiological parameter of the patient during the time the patient is in contact with the contact point and when the control module detects a current flow through the patient.

Notwithstanding the claims and the above aspects of the present invention, in various other aspects, the present invention also may be defined by the following clauses:

1. A computer system to track medication from manufacturer to a patient, to enable a care provider to determine the origin of the medication and to confirm that at least one of the right type and the right dosage of medication was delivered to the patient, the computer system comprising:
   a processor operative to:
   receive a unique identity of an identifier device secured to a dosage of medication to confirm the origin of the medication and the type of the medication, wherein the identifier device comprises the unique identity that is associated with at least one of the manufacturer and the medication;
   receive information from a patient interface device in communication with the computer and the patient, wherein at the time the patient takes the medication, the patient interface device is operative to detect the unique identity associated with the identifier device and confirm delivery of the medication to the patient; and
   receive the detected unique identity associated with the identifier device detected from the patient interface device and the confirmation of delivery of the medication to the patient from the patient interface device.

2. The computer system of clause 1, wherein the processor is operative to interrogate the identifier device.

3. The computer system of clause 1 or 2, wherein the identifier device comprises a tag provided with circuitry, wherein the tag is secured to the dosage of the medication, and wherein the processor is operative to read the unique identity from the tag.

4. The computer system of any of the preceding clauses, wherein the tag is secured to a dosage of medication in the form of a pill.

5. The computer system of any of the preceding clauses 1-3, wherein the tag is secured to a syringe configured for delivery of the dosage of medication, wherein the syringe comprises a safety component which is activated upon exposure to air.

6. The computer system of clause 5, wherein the syringe comprises a needle and wherein the needle comprises at least one contact point coupled to the tag.

7. The computer system according to any of the preceding clauses wherein the processor is operative to communicate with a datacenter database to at least one of retrieve medical information about the patient and provide information related to the medication to be administered to the patient.

8. The computer system of clause 7, wherein the processor is operative to:
   communicate with at least one of a database or a processing system at the datacenter;
   transmit information to the processing system;
   receive information from the processing system, wherein the processing system is operative to access the information in the database of the data center and provide the information to the patient through the computer.

9. The computer system according to any of the preceding clauses wherein the processor is operative to validate at least one of the type and dosage selected by the care provider prior to dispensing the medication to the patient.

10. The computer system according to any of the preceding clauses wherein the processor is operative to communicate with an interrogation unit coupled to the identifier device, wherein the interrogation unit is operative to interrogate the identifier device secured to the medication and receive the unique identity of the identifier device to confirm the origin of the medication and the type of the medication, wherein the computer is operative to interrogate the interrogation unit and receive the unique identity of the identifier from the interrogation unit.

11. The computer system of clause 10, wherein the processor is operative to:
   communicate with a memory of the interrogation unit; and
   receive the unique identity of the identifier stored in the memory of the interrogation unit.

12. The computer system according to any of the preceding clauses wherein the processor is operative to receive biometric parameters from the patient interface device, wherein the biometric parameters can identify the patient, or wherein the processor is operative to receive an image of the patient captured by a camera on the patient interface device.

13. The computer system according to any of the preceding clauses comprising a display to provide information associated with the patient, wherein the information comprises any of an image of the patient, medical history of the patient, and a next type and dose of medication to deliver to the patient.

14. A computer-implemented method to track medication from manufacturer to a patient, which preferably uses a computer system according to any of the preceding clauses, to enable a care provider to determine the origin of the medication and to confirm that at least one of the right type and the right dosage of medication was delivered to the patient, the computer comprising a processor, the method comprising:
   receiving by the processor a unique identity of the identifier device secured to a dosage of medication to confirm the origin of the medication and the type of the medication, wherein the identifier device comprises the unique identity that is associated with at least one of the manufacturer and the medication;

receiving by the processor information from a patient interface device in communication with the computer and the patient, wherein at the time the patient takes the medication, the patient interface device is operative to detect the unique identity associated with the identifier device and confirm delivery of the medication to the patient; and receiving by the processor the detected unique identity associated with the identifier device detected from the patient interface device and the confirmation of delivery of the medication to the patient from the patient interface device.

15. The computer-implemented method of clause 15, comprising interrogating by the processor the identifier device.

16. The computer-implemented method of clause 14 or 15, comprising receiving by the processor the unique identity from a tag, wherein the identifier device comprises the tag provided with circuitry, wherein the tag is secured to the dosage of the medication, the method.

17. The computer-implemented method of clause 16, comprising receiving by the processor the unique identity from the tag, wherein the tag is secured to a dosage of medication in the form of a pill or wherein the tag is secured to a syringe configured for delivery of the dosage of medication, wherein the syringe comprises a safety component which is activated upon exposure to air, preferably comprising receiving by the processor the unique identity from the tag, wherein the syringe comprises a needle, and wherein the needle comprises at least one contact point coupled to the tag.

18. The computer-implemented according to any of the clauses 14-17 comprising at least one of:

retrieving by the processor medical information about the patient from a datacenter database; and providing by the processor information related to the medication to be administered to the patient.

19. The computer-implemented method of clause 18, comprising:

transmitting by the processor information to the processing system; receiving by the processor information from the processing system, wherein the processing system is operative to access the information in the database of the data center and provide the information to the patient through the computer.

20. The computer-implemented method according to any of the clauses 14-19, comprising:

validating by the processor at least one of the type and dosage selected by the care provider prior to dispensing the medication to the patient.

21. The computer-implemented method according to any of the clauses 14-20 comprising:

interrogating by the processor operative an interrogation unit coupled to the identifier device, wherein the interrogation unit is operative to interrogate the identifier device secured to the medication and receive the unique identity of the identifier device to confirm the origin of the medication and the type of the medication; and receiving by the computer the unique identity of the identifier from the interrogation unit.

22. The computer-implemented method of clause 21, comprising:

communicating by the processor with a memory of the interrogation unit; and receiving by the processor the unique identity of the identifier stored in the memory of the interrogation unit.

23. The computer-implemented method according to any of the clauses 14-22 comprising:

receiving by the processor biometric parameters from the patient interface device, wherein the biometric parameters can identify the patient.

24. The computer-implemented method according to any of the clauses 14-23 comprising:

receiving by the processor an image of the patient captured by a camera on the patient interface device.

25. The computer-implemented method according to any of the clauses 14-24 comprising:

displaying on a display coupled to the processor information associated with the patient, wherein the information comprises any of an image of the patient, medical history of the patient, and a next type and dose of medication to deliver to the patient.

26. An apparatus, comprising:

at least one contact point configured to electrically engage an identifier device secured to a medication, wherein the identifier device comprises a unique identity that is associated with at least one of the manufacturer and the medication;

an interrogation unit coupled to the at least one contact point, wherein the interrogation unit is operative to interrogate the identifier device to obtain the unique identity; and a communication module coupled to the interrogation unit, wherein the communication module is operative to transmit the unique identification.

27. The apparatus of clause 26, wherein the interrogation unit is operative to read the unique identity associated with the identifier device.

28. The apparatus of clause 26 or 27 wherein the communication module is operative to transmit the unique identity associated with the identifier device to a computer in communication with the communication module.

29. The apparatus according to any of the clauses 26-28 comprising a memory coupled to the interrogation unit to store the unique identity associated with the identifier device.

30. The apparatus according to any of the clauses 26-29 wherein the interrogation unit is operative to read the unique identity from a tag provided with circuitry, wherein the tag is secured to the dosage of the medication, preferably wherein the interrogation unit is operative to read the unique identity from the tag, wherein the tag is secured to a dosage of medication in the form of a pill, or wherein the interrogation unit is operative to read the unique identity from the tag, wherein the tag is secured to a syringe configured for delivery of the dosage of medication, wherein the syringe comprises a safety component which is activated upon exposure to air, preferably wherein the syringe comprises a needle and wherein the needle comprises at least one contact point coupled to the tag.

31. A method, comprising:

electrically engaging by an interrogation unit an identifier device secured to a medication with at least one contact point coupled to the interrogation unit, wherein the identifier device comprises a unique identity that is associated with at least one of the manufacturer and the medication;

interrogating the identifier device for the unique identity; and transmitting the unique identification by a communication module coupled to the interrogation unit.

32. The method of clause 31, comprising reading by the interrogation unit the unique identity associated with the identifier device.

33. The method of clause 31 or 32 comprising transmitting by the communication module the unique identity associated with the identifier device to a computer in communication with the communication module.

34. The method according to any of the clauses 31-33 comprising storing by the interrogation unit the unique identity associated with the identifier device in a memory, wherein the memory is coupled to the interrogation unit.

35. The method according to any of the clauses 31-34 comprising receiving by the interrogation unit the unique identity from a tag, wherein the identifier device comprises the tag provided with circuitry, wherein the tag is secured to the dosage of the medication.

36. The method of clause 35, comprising receiving by the interrogation unit the unique identity from the tag, wherein the tag is secured to a syringe configured for delivery of the dosage of medication, wherein the syringe comprises a safety component which is activated upon exposure to air, preferably wherein the syringe comprises a needle, and wherein the needle comprises at least one contact point coupled to the tag.

37. A patient interface device, comprising:
a housing defining an outer surface, wherein the housing is configured to held by a patient;
at least one contact point exposed on the outer surface portion of the housing, wherein the at least one contact point is positioned to be physically contacted by the patient to detect biometric information associated with the patient, wherein the at least one contact point is configured to detect at least one physiological parameter associated with the patient;
a control module coupled to the at least one contact point, wherein the at least one contact point is coupled to the control module to capture the at least one physiological parameter associated with the patient; and
a communication module coupled to the control unit to transmit the at least one physiological parameter to a computer in communication with the communication module.

38. The patient interface device of clause 37, comprising a power source coupled to the control module.

39. The patient interface device of clause 37 or 38 comprising an image generation unit to capture an image of the patient, wherein the image generation unit is coupled to the control module and is configured to capture the image of the patient and to transmit the captured image to the control module.

40. The patient interface device according to any of the clauses 37-39 wherein the control module is operative to activate the image generation unit to capture the image of the patient when the contact point detects there is a change in the physiological parameter of the patient during the time the patient is in contact with the contact point and when the control module detects a current flow through the patient.

41. A method, comprising:
contacting by a patient at least one contact point exposed on an outer surface portion of a housing, wherein the at least one contact point is positioned to be physically contacted by the patient to detect biometric information associated with the patient, wherein the at least one contact point is configured to detect at least one physiological parameter associated with the patient;
capturing by a control module coupled to the at least one contact point at least one physiological parameter associated with the patient; and
transmitting by a communication module coupled to the control unit the at least one physiological parameter to a computer in communication with the communication module.

42. The method of clause 41, comprising:
scanning by the at least contact point a fingerprint associated with the patient;
confirming by the control module fingerprint information.

43. The method of clause 41 or 42, comprising:
capturing an image of the patient by an image generation unit, wherein the image generation unit is coupled to the control module; and
transmitting by the image generation unit the captured image of the patient to the control module.

44. The method according to any of the clauses 41-43 comprising activating by the control module the image generation unit to capture the image of the patient when the contact point detects there is a change in the physiological parameter of the patient during the time the patient is in contact with the contact point and when the control module detects a current flow through the patient.

45. System for tracking a product from a manufacturer along a supply chain to a user, the system comprising:
Identifying means associated with the product for identifying the product,
Interrogating means for interrogating the identifying means.

46. System according to clause 45 wherein the product is a medicine and the user is a patient, wherein the system enables a care provider to determine the origin of the medicine.

47. System according to clause 45 or 46, further comprising patient communication means for communicating identity of the medicine to the patient.

48. System according to any of the preceding clauses 45-47 wherein the identifying means comprises a device secured to the product.

49. System according to clause 48, wherein the identifying means has a unique identity associated with the manufacturer and/or the product.

50. System according to any of the preceding clauses 46-49 wherein the system confirms that a correct dosage and/or correct type of medication was delivered to the patient.

51. System according to any of the preceding clauses 45-50 wherein the interrogating means comprises a computer system which reads the unique identity of the identifying means.

52. System according to clause 51 wherein the computer system communicates with a database to retrieve user information and/or product information.

53. System according to clauses 52 wherein the user information is patient information, and wherein the product information is information related to the medicament to be administered to the patient.

54. System according to any of the clauses 51-53 wherein the computer system validates at least one of the type and dosage prior to dispensing.

55. System according to any of the preceding clauses 47-54, wherein the patient communication means is configured to be in physical communication with the patient at the time the patient takes the medication, and is in communication with the computer system, the patient communication means being a personal device which detects the unique identity of the identifying means and confirms delivery of the product.

56. System according to any of the preceding clauses 45-55 wherein the identifying means is a tag provided with circuitry, which tag is secured to a pill, and which circuitry is broken if the tag is removed from the pill.

57. System according to any of the preceding clauses 45-55 wherein the identifying means is a tag, which tag is secured to a syringe, wherein the tag and/or syringe comprises a safety component which is activated on exposure to air.

58. System according to clauses 56 or 57 wherein the tag cannot be interrogated if the medicament is not delivered within a pre-determined time period.

59. System according to clauses 57 or 58 wherein a needle of the syringe includes a contact point connected to the tag.

60. An interface device for confirming delivery of medication to a patient, preferably for use in a system according to any of the preceding clauses 45-59, the device comprising:
a control module, wherein the control modules includes a communication module and a memory unit;
   a contact point to detect at least one physiological parameter associated with the patient, wherein the contact point is connected to the control module and captures at least one physiological parameter associated with the patient and transmits that information to the patient; and
   an image generation unit to capture the patient's image, wherein the image generation unit is connected to the control module and captures the image of the patient and transmits the image to the control module,
   wherein the control module activates the image generation unit to capture the image of the patient when the contact point detects there is a change in the physiological parameter of the patient during the time the patient is in contact with the contact point and when the control module detects a current flow through the patient.

61. System according to any of the preceding clauses 45-59, further comprising a device according to clause 60.

62. Method for tracking a product from a manufacturer along a supply chain to a user comprising the steps of attaching identifying means to a product, and interrogating the identifying means.

63. Method according to clause 62 further comprising the step of confirming receipt of the product to the user.

64. Method according to clause 62 or 63 using a system, device or apparatus according to any of the preceding.

65. A pill comprising a tag, which tag is provided with circuitry.

66. A syringe comprising a tag, wherein the tag and/or syringe comprises a safety component which is activated on exposure to air.

67. System to track medication from manufacturer to a patient, to enable a care provider to determine the origin of the medication and to confirm that at least one of the right type and the right dosage of medication was delivered to the patient, the system comprising:
   an identifier device secured to the medication, wherein the identifier device has a unique identity that is associated with at least one of the manufacturer and the medication;
   a computer system for interrogating the identifier device,
      wherein the computer system reads the unique identity of the identifier device to confirm the origin of the medication and the type of the medication and
      wherein the computer system communicates with a database to at least one of retrieve medical information about the patient and provide information related to the medication to be administered to the patient and
      wherein the computer system validates at least one of the type and dosage selected by the care provider prior to dispensing to the patient; and
   a personal device in communication with the computer system, wherein the personal device is configured to be in physical communication with the patient at the time the patient takes the medication to detect the unique identity associated with the identifier device and confirm delivery of the medication to the patient.

68. Method to track and guide a care provider to deliver a proper type and dose of medication to a patient such that a care provider confirms that the medication is traceable to a known origin, the method comprising the steps of:
   attaching an identifiable tag that produces a unique signature to the medication at the origin when the medication is created;
   interrogating the tag at about the time of delivery to the patient to determine if the medication is the original medication and to confirm that that the correct medication has been selected for the patient; and
   confirming that the patient has taken or received the medication through detecting the identifiable tag's unique signature through the patient's body based on communication of the identifiable tag with the patient.

69. System to track a deliverable to a user, the system comprising:
   an identifier device secured to the deliverable, wherein the identifier device has a unique identity that is associated with the deliverable;
   a computer system for interrogating the identifier device,
      wherein the computer system identifies the identifier device to confirm information associated with the deliverable and
      wherein the computer system communicates with a database to at least one of retrieve information associated with the user and provide a care provider with the information associated with the deliverable to be administered to the user and
      wherein the computer system validates the information associated with the deliverable provided by the care provider prior to administration to the user; and
   a personal device in communication with the computer system, wherein the personal device is configured to be held by the user at the time the user is administered the deliverable to detect the unique identity associated with the identifier device and to confirm delivery of the deliverable to the user.

70. Method to track and guide a care provider to deliver a deliverable to a user such that the care provider can confirm that the deliverable is traceable to a known origin, the method comprising the steps of:
   providing an identifiable tag that produces a unique signature, the identifiable tag physically associated with the deliverable;
   interrogating an identifiable tag associated with the deliverable at about the time of delivery to the user to determine if the deliverable is the intended deliverable and confirm that the care provider has selected the correct deliverable; and
   confirming that the user has been administered the deliverable through detecting the identifiable tag's unique signature based on contact of the identifiable tag with the user.

71. Interface device for confirming delivery of medication to a patient, the device comprising:
   a control module, wherein the control modules includes a communication module and a memory unit;
   a contact point to detect at least one physiological parameter associated with the patient, wherein the contact point is connected to the control module and captures at least one physiological parameter associated with the patient and transmits that information to the patient; and
   an image generation unit to capture the patient's image, wherein the image generation unit is connected to the control module and captures the image of the patient and transmits the image to the control module, wherein the control module activates the image generation unit to capture the image of the patient when the contact point detects there is a change in the physiological parameter of the patient during the time the patient is in contact with the contact point and when the control module detects a current flow through the patient.

DETAILED DESCRIPTION

Figure 1:
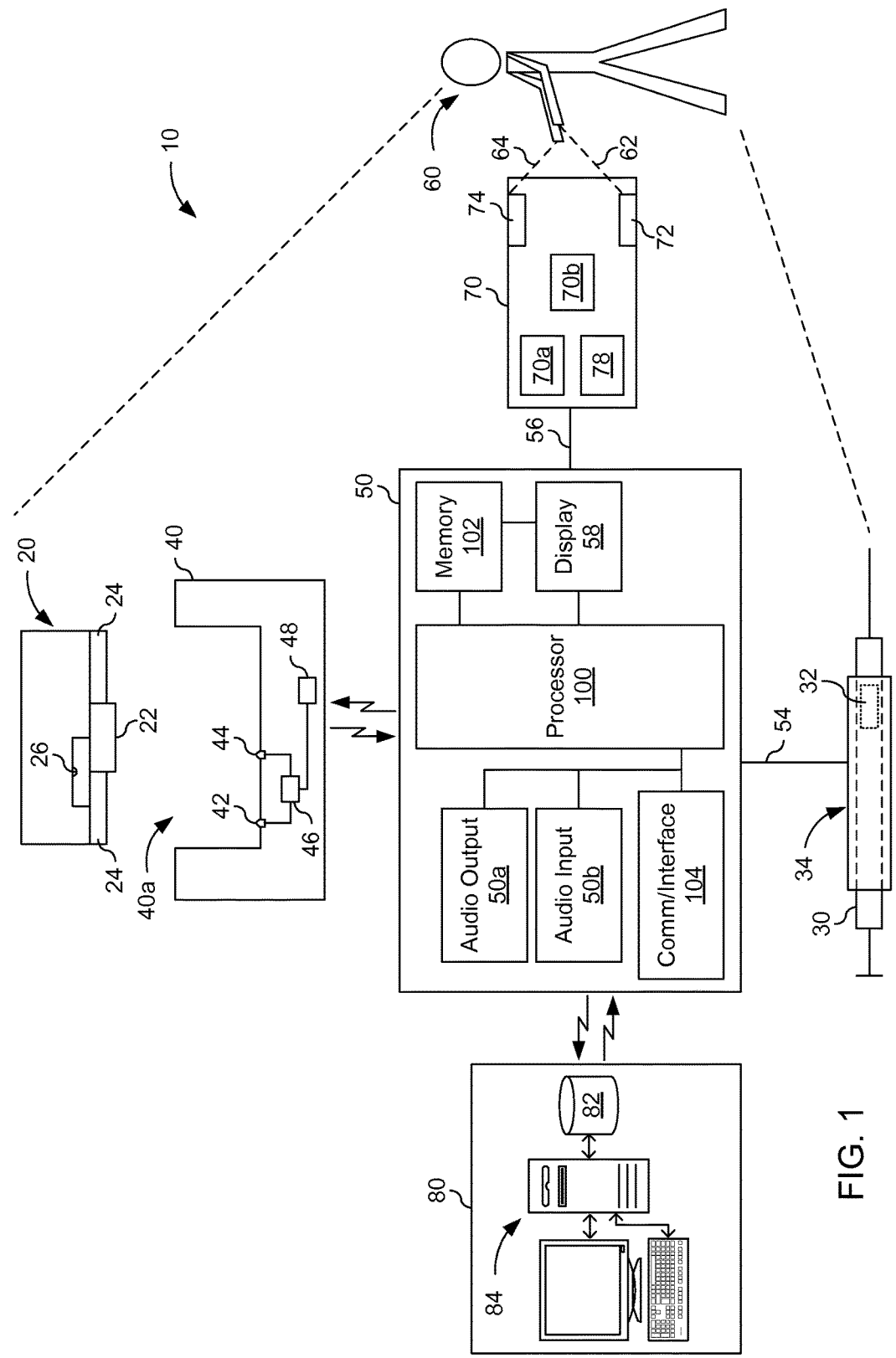
FIG. 1 shows a system for tracking medication from origin to patient as well as confirmation of delivery of the correct type and dose of medication.

Referring now to FIG. 1, a system 10 includes a device 40, a mobile computer 50, and a patient identity confirmation device 70. The system 10 communicates with a central data center 80. In accordance with various aspects of the present invention, there are at least two methods disclosed for delivery of medication: a pill 20 and a syringe 30.

However, the scope of the present invention is not limited by delivery methods used. For example, the medication may be delivered by a patch, an inhaler, or an ointment. Further, the term "pill" includes various form factors of ingestible medicaments and carriers, e.g., capsules, gel caps, placebos, over capsulation carriers or vehicles, etc. In the event a patch is used, then the tag can be secured to the patch. If an ointment is used, then the tag may be included with ointment and delivery and tracking can be confirmed once the ointment is applied. At the origin or location of manufacturing of the medication, an identifiable tag is associated with the medication regardless of the type of medication or method of delivery/dispensing of the medication to the patient. The identifiable tag is similar to an ingestible event marker or an ionic emission module (IEM). The IEM can be ingested and is capable of providing an identifiable signature and is unique. The IEM is disclosed in greater detail in U.S. patent application Ser. No. 12/564,017 entitled COMMUNICATION SYSTEM WITH PARTIAL POWER SOURCE filed on Sep. 21, 2009, and published as 2010-0081894 A1 dated Apr. 1, 2010, which is incorporated herein by reference in its entirety.

In accordance with other aspects of the present invention, the identifiable tags may include bar codes on packaging that uniquely identify the medication in the package, which package includes tamper proof seals. Thus the care provider would use the mobile computer 50 to scan the bar code or capture an image of the bar code that is transmitted to the data center 80 for confirmation.

With respect to the pill 20, an identifiable tag 22 is shown secured to one side of the pill 20. Surrounding the tag 22 is a conducting surface 24. One surface of the tag 22 is exposed and the other surface of the tag 22 is electrically coupled to the surface 24 via a conduction path 26. The conducting surface 24 can be created using a variety of techniques, e.g., any ingestible conducting ink technology. To prevent removal of the tag 22 from the pill 20, the tag 22 is secured in such a way to cause destruction of the circuitry of the tag 22 if attempts are made to separate it from the medication. Additionally, including the conducting surface 24 around the tag 22 further prevents tampering with and removal of the tag 22. Specifically, if the tag 22 is removed from the pill 20, then the conducting surface 24 and the path 26 will be separated from the tag 22 thereby preventing interrogation of the tag 22 by a device 40.

The device 40 includes contact points 42 and 44, each of which is connected to an interrogation unit 46. The device 40 also includes a power source, which is not shown. The interrogation unit 46 is connected to a communication module 48. To confirm the origin of the pill 20 as well the type and dose, the pill 20 is placed in the opening 40a and comes into contact with contact points 42 and 44. The interrogation unit 46 can then read the identity of the tag 22. The identity of the tag 22 is then communicated to a mobile computer 50. The communication link 52 between the device 40 and the mobile computer 50 is any wireless communication link, such as Bluetooth™ technology or similar wireless technology. In another aspect, the device 40 may be part of the computer 50 as well.

According to another aspect of the present invention, the device 40 may include a memory for storing the information for later transmission or communication as well as confirmation in the event the communication link between the device 40 and the mobile computer 50 is interrupted or lost.

Additionally, in accordance with another aspect of the present invention, the device 40 may be directly connected to the mobile computer 50 with a physical link (not shown), such as a wired connection, such as a Universal Serial Bus (USB). The mobile computer 50 is then able to confirm the origin of the medication and other information associated with correct delivery of the type and dose of medication to a patient 60. The computer 50 is shown with a display 58. The display 58 can provide information such as an image of the patient, patient's medical history, the next type and dose of medication to deliver to the patient. In accordance with various aspects of the present invention, the mobile computer 50 may be any device that includes a display and wireless communication capabilities, such as a mobile communication device, a mobile phone, or a laptop computer with wireless communication unit. Furthermore, the mobile computer 50 includes audio output 50a and an audio input 50b, which can be used together to simulate a modem and create a data channel for communication. Also, the mobile computer 50 is capable of communication using various communications protocol(s), e.g., Short Message Service (SMS) such that information is transmitted to a destination through mobile phone communication channels.

With respect to the syringe 30, an identifiable tag 32 is secured to the syringe 30. To ensure that the tag 32 cannot be removed from the syringe 30 and reattached to a different syringe, the syringe and/or tag include(s) a safety component, e.g., the tag 32 includes a layer that is activated once exposed to air, such as a zinc battery. Thus, upon manufacture, each syringe 30 is secured within a hermetically sealed package to preserve the tag 32. Once the package is opened, the tag 32 is exposed to the air and, hence, activated. Thus, if the package is opened and the medication is not delivered within a short period of time, such a few minutes, then the tag 32 is deactivated and cannot be interrogated later. In accordance with one aspect of the present invention, the layer of the tag 32 is a zinc-based battery that is activated upon contact with the surrounding air and, hence, powers up the tag 32.

Once the syringe 30 is removed from the package and the care provider is ready to deliver the medication to the patient, the syringe 30 is placed inside the sleeve 34. The sleeve 34 can detect and capture the identity of the tag 32. The sleeve 34 transmits the information associated with the tag 32 secured to the syringe 30 via a physical connection 54 between the mobile computer 50 and the sleeve 34. In accordance with another aspect of the present invention, the sleeve 34 may be in communication with the mobile computer 50 via a wireless connection, not shown. As the needle of the syringe 30 comes into contact with the patient 60, then the circuit is completed as shown through the patient identity confirmation device 70.

Figure 2A:
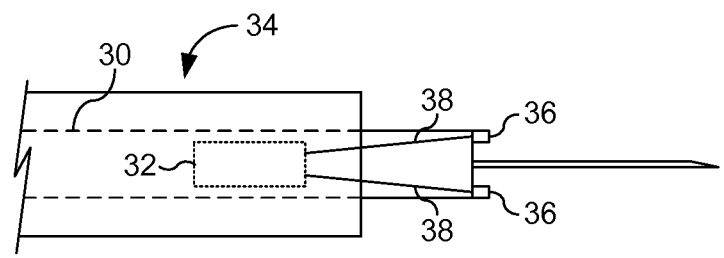
FIG. 2A shows a needle of a syringe used for delivery of medication in accordance with one aspect of the present invention.
Figure 2B:
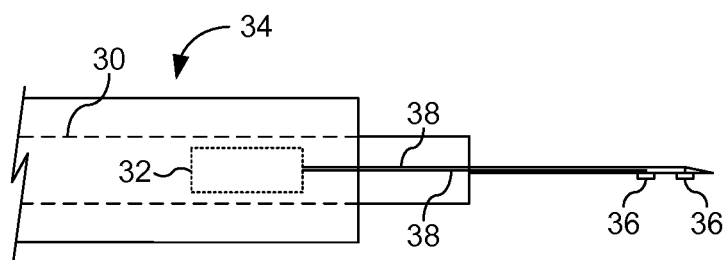
FIG. 2B shows a needle of a syringe used for delivery of medication in accordance with another aspect of the present invention.

Referring now to FIG. 2A and FIG. 2B, in accordance with another aspect of the present invention, the needle of the syringe 30 may include specific contact points 36 that are connected to the tag 32 via connection 38. The contact points 36 are positioned along at the end of the syringe 30 or on the needle such that contact with the skin of the patient completes a circuit that is then used to activate the tag 32 to transmit a unique signature or identity that represents delivery of the medication to the patient 60.

Figure 2C:
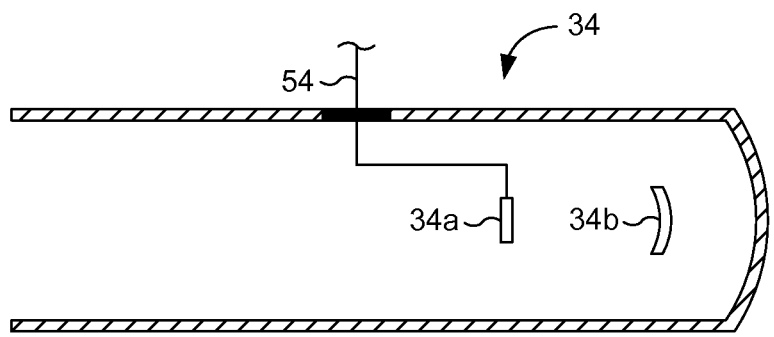
FIG. 2C shows a cut-away section of a sleeve for holding the syringe of FIG. 2A and FIG. 2B in accordance with an aspect of the present invention.

Referring now to FIG. 2C, the contact points 36 are electrically coupled to the tag 32. The tag 32 is electrically coupled to the sleeve 34 as the syringe 30 is placed inside the sleeve 34 through a contact point 34a. The contact point 34a makes contact with the tag 32 to allow electrical signals to pass between the tag 32, through the connection 54, and the mobile computer 50. A stop tab 34b is positioned within the sleeve 34 to ensure proper alignment of the contact point 34a with the tag 32.

Figure 3:
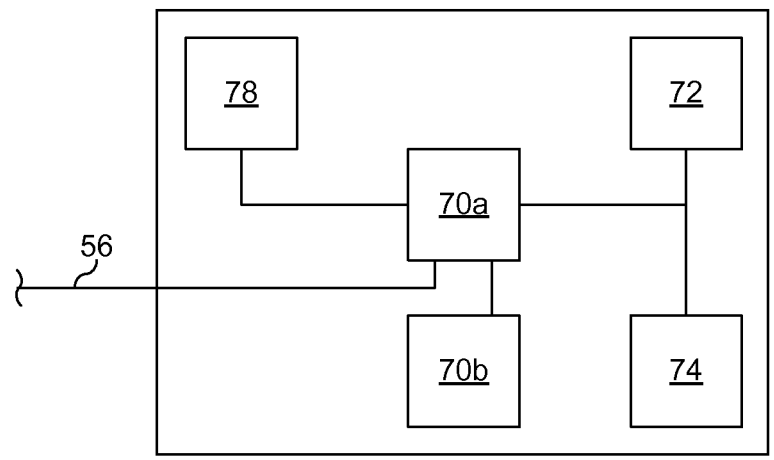
FIG. 3 shows a functional block diagram representation of an identity confirmation device as used in FIG. 1 in accordance with one aspect of the present invention.

Referring now to FIG. 1 and FIG. 3, the patient identity confirmation device 70 is shown connected to the mobile computer 50 via a connection or link 56. The patient identity confirmation device 70 includes thumb pads or contact points 72 and 74 exposed on the surface of the patient identity confirmation device 70. The contact points 72 and 74 may be any form of biometric detection contacts in accordance with various aspects of the present invention. For example, the contact point may scan and confirm fingerprint information. In accordance with another aspect of the present invention, the contact points may detect the physiological parameters of the patient, such as temperature, or other biometric parameters that can identify the patient, including DNA. The contact points 72 and 74 are electrically coupled to a control unit 70a within the patient identity confirmation device 70. In accordance with one aspect of the present invention, a power source 70b is electrically coupled to the control unit 70a, so that the patient identity confirmation device 70 is self powered. In accordance with another aspect of the present invention, the patient identity confirmation device 70 can receive power from the mobile computer through the connection 56.

In accordance with one aspect of the present invention, the patient identity confirmation device 70 includes a camera 78 for capturing an image of the patient that is transmitted to the mobile computer 50. The camera 78 is electrically connected to the control unit 70a. The control unit 70a controls the activation of the camera 78 once the control unit 70a detected that a circuit path is complete, which indicates that the patient 60 is receiving the medication. More specifically, the patient 60 holds the patient identity confirmation device 70 using at least one of the contact points 72 and 74 to create a physical connection between the patient identity confirmation device 70 and the patient 60 at one of the limbs 62 and 64, e.g., right and left thumbs. As the patient 60 holds the patient identity confirmation device 70 and the syringe 30 comes into contact with the patient 60, then a circuit is completed. More specifically, the contact points 36 come into contact with the skin of the patient 60. The contact points 36 are electrically coupled to the tag 32 and the tag 32 is electrically coupled to the sleeve 34. The sleeve 34 is electrically coupled to the mobile computer 50 and the mobile computer 50 is electrically coupled to the patient identity confirmation device 70. Thus, a complete circuit is formed through the patient 60 once the patient hold the patient identity confirmation device 70 and the needle of the syringe 30 comes into contact with the skin of the patient 60.

As indicated above the contact points 72 and 74 can detect physiological parameters of the patient through the physical contact, including a change in heart rate, which is typical when the needle of the syringe 30 pierces the skin of patient 60. This change in physiological parameter of the patient 60 can be a trigger that is used by the control unit 70a to activate the camera to capture an image of the patient 60. The information associated with the time and date of delivery as well as the image of the patient 60 is sent to the mobile computer 50. The mobile computer 50 can record the delivery of the medication to the patient 60. Additionally, the mobile computer 50 can scan or interrogate the tag 32 to confirm the dose and type of medication delivered. Thereafter, the zinc-based layer of the tag 32 expires and the tag 32 cannot be used again. In accordance with another aspect of the present invention, the syringe 30 may be a single use syringe such that once the plunger is depressed, it cannot be retracted or extracted.

Figure 4:
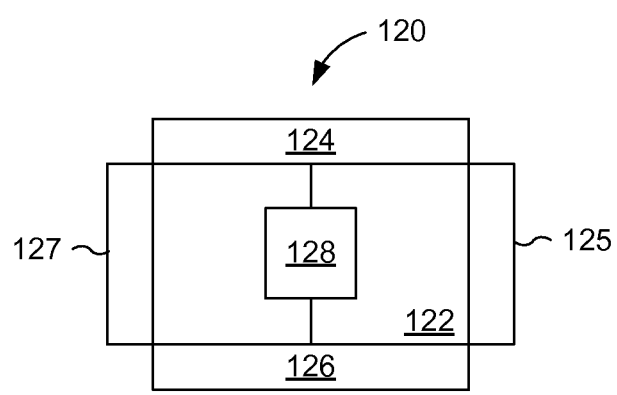
FIG. 4 shows one aspect of a tag.

In various aspects the identifiable tags 22, 32, similar to an ingestible event marker or an ionic emission module (IEM), may be implemented in accordance with the system 120 shown in FIG. 4. The system 120 can be used in association with any medication product, as mentioned above, to determine the origin of the medication and to confirm that at least one of the right type and the right dosage of medication was delivered to the patient and in some aspects to determine when a patient takes the pharmaceutical product. The scope of the present disclosure, however, is not limited by the environment and the product that is used with the system 120. For example, the system may be activated either in wireless mode, in galvanic mode by placing the system 120 within a capsule and the placing the capsule within the conducting fluid, or a combination thereof, or exposing the system 120 to air. Once placed in a conducting fluid, for example, the capsule would dissolve over a period of time and release the system 120 into the conducting fluid. Thus, in one aspect, the capsule would contain the system 120 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 120 may be ingested at the same time that any pharmaceutical product is ingested in order to record the occurrence of the event, such as when the product was taken.

In the specific example of the system 120 combined with a medication or pharmaceutical product, as the product or pill is ingested, or exposed to air, the system 120 is activated in galvanic mode. The system 120 controls conductance to produce a unique current signature that is detected, thereby signifying that the pharmaceutical product has been taken. When activated in wireless mode, the system controls modulation of capacitive plates to produce a unique voltage signature associated with the system 120 that is detected.

In one aspect, the system 120 includes a framework 122. The framework 122 is a chassis for the system 120 and multiple components are attached to, deposited upon, or secured to the framework 122. In this aspect of the system 120, a digestible material 124 is physically associated with the framework 122. The material 124 may be chemically deposited on, evaporated onto, secured to, or built-up on the framework all of which may be referred to herein as "deposit" with respect to the framework 122. The material 124 is deposited on one side of the framework 122. The materials of interest that can be used as material 124 include, but are not limited to: Cu, CuCl, or CuI. The material 124 is deposited by physical vapor deposition, electrodeposition, or plasma deposition, among other protocols. The material 124 may be from about 0.05 to about 500 µm thick, such as from about 5 to about 100 µm thick. The shape is controlled by shadow mask deposition, or photolithography and etching. Additionally, even though only one region is shown for depositing the material, each system 120 may contain two or more electrically unique regions where the material 124 may be deposited, as desired.

At a different side, which is the opposite side as shown in FIG. 4, another digestible material 126 is deposited, such that the materials 124 and 126 are dissimilar and insulated from each other. Although not shown, the different side selected may be the side next to the side selected for the material 124. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 124 and 126 are selected such that they produce a voltage potential difference when the system 120 is in contact with conducting liquid, such as body fluids. The materials of interest for material 126 include, but are not limited to: Mg, Zn, or other electronegative metals. As indicated above with respect to the material 124, the material 126 may be chemically deposited on, evaporated onto, secured to, or built-up on the framework. Also, an adhesion layer may be necessary to help the material 126 (as well as material 124 when needed) to adhere to the framework 122. Typical adhesion layers for the material 126 are Ti, TiW, Cr or similar material. Anode material and the adhesion layer may be deposited by physical vapor deposition, electrodeposition or plasma deposition. The material 126 may be from about 0.05 to about 500 µm thick, such as from about 5 to about 100 µm thick. However, the scope of the present disclosure is not limited by the thickness of any of the materials nor by the type of process used to deposit or secure the materials to the framework 122.

According to the disclosure set forth, the materials 124 and 126 can be any pair of materials with different electrochemical potentials. Additionally, in the embodiments wherein the system 120 is used in-vivo, the materials 124 and 126 may be vitamins that can be absorbed. More specifically, the materials 124 and 126 can be made of any two materials appropriate for the environment in which the system 120 will be operating. For example, when used with an ingestible product, the materials 124 and 126 are any pair of materials with different electrochemical potentials that are ingestible. An illustrative example includes the instance when the system 120 is in contact with an ionic solution, such as stomach acids. Suitable materials are not restricted to metals, and in certain embodiments the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In one embodiment, one or both of the metals may be doped with a non-metal, e.g., to enhance the voltage potential created between the materials as they come into contact with a conducting liquid. Non-metals that may be used as doping agents in certain embodiments include, but are not limited to: sulfur, iodine, and the like. In another embodiment, the materials are copper iodine (CuI) as the anode and magnesium (Mg) as the cathode. Aspects of the present disclosure use electrode materials that are not harmful to the human body.

TABLE 1

| | Anode | Cathode |
|---|---|---|
| Metals | Magnesium, Zinc Sodium (†), Lithium (†) Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

Thus, when the system 120 is in contact with the conducting fluid, a current path is formed through the conducting fluid between the dissimilar materials 124 and 126. A control device 128 is secured to the framework 122 and electrically coupled to the materials 124 and 126. The control device 128 includes electronic circuitry, for example control logic that is capable of controlling and altering the conductance between the materials 124 and 126.

The voltage potential created between the dissimilar materials 124 and 126 provides the power for operating the system as well as produces the current flow through the conducting fluid and the system 120. In one aspect, the system 120 operates in direct current mode. In an alternative aspect, the system 120 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 124 and 126 is completed external to the system 120; the current path through the system 120 is controlled by the control device 128. Completion of the current path allows for the current to flow and in turn a receiver, not shown, can detect the presence of the current and recognize that the system 120 has been activate and the desired event is occurring or has occurred.

In one embodiment, the two dissimilar materials 124 and 126 are similar in function to the two electrodes needed for a direct current power source, such as a battery. The conducting liquid acts as the electrolyte needed to complete the power source. The completed power source described is defined by the physical chemical reaction between the dissimilar materials 124 and 126 of the system 120 and the surrounding fluids of the body. The completed power source may be viewed as a power source that exploits reverse electrolysis in an ionic or a conduction solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 124 and 126 are shielded from the surrounding environment by an additional layer of material. Accordingly, when the shield is dissolved and the two dissimilar materials 124, 126 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain embodiments, electrode materials are chosen to provide for a voltage upon contact with the target physiological site, e.g., the stomach, sufficient to drive the system of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Referring still to FIG. 4, the dissimilar materials 124 and 126 provide the voltage potential to activate the control device 128. Once the control device 128 is activated or powered up, the control device 128 can alter conductance between the first and second materials 124 and 126 in a unique manner. By altering the conductance between the first and second materials 124 and 126, the control device 128 is capable of controlling the magnitude of the current through the conducting liquid that surrounds the system 120. This produces a unique current signature that can be detected and measured by a receiver (not shown), which can be positioned internal or external to the body. The receiver is disclosed in greater detail in U.S. patent application Ser. No. 12/673,326 entitled BODY-ASSOCIATED RECEIVER AND METHOD filed on Dec. 15, 2009, and published as 2010-0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, the entire content of which is incorporated herein by reference. Alternatively, throughout the disclosure herein, the terms "non-conducting material," "membrane," and "skirt" are interchangeably used with the term "current path extender" without impacting the scope or the present embodiments and the claims herein. The skirt, shown in portion at 125 and 127, respectively, may be associated with, e.g., secured to, the framework 122. Various shapes and configurations for the skirt are contemplated as within the scope of the various aspects of the present invention. For example, the system 120 may be surrounded entirely or partially by the skirt and the skirt maybe positioned along a central axis of the system 120 or off-center relative to a central axis. Thus, the scope of the present invention as claimed herein is not limited by the shape or size of the skirt. Furthermore, in other embodiments, the dissimilar materials 124 and 126 may be separated by one skirt that is positioned in any defined region between the dissimilar materials 124 and 126.

The system 120 may be grounded through a ground contact. The system 120 also may include a sensor module. In operation, ion or current paths are established between the first material 124 to the second material 126 and through a conducting fluid in contact with the system 120. The voltage potential created between the first and second materials 124 and 126 is created through chemical reactions between the first and second materials 124/126 and the conducting fluid. In one aspect, the surface of the first material 124 is not planar, but rather an irregular surface. The irregular surface increases the surface area of the material and, hence, the area that comes in contact with the conducting fluid.

In one aspect, at the surface of the first material 124, there is chemical reaction between the material 124 and the surrounding conducting fluid such that mass is released into the conducting fluid. The term mass as used herein refers to protons and neutrons that form a substance. One example includes the instant where the material is CuCl and when in contact with the conducting fluid, CuCl becomes Cu (solid) and Cl— in solution. The flow of ions into the conduction fluid is via ion paths. In a similar manner, there is a chemical reaction between the second material 126 and the surrounding conducting fluid and ions are captured by the second material 126. The release of ions at the first material 124 and capture of ion by the second material 126 is collectively referred to as the ionic exchange.

The rate of ionic exchange and, hence the ionic emission rate or flow, is controlled by the control device 128. The control device 128 can increase or decrease the rate of ion flow by altering the conductance, which alters the impedance, between the first and second materials 124 and 126. Through controlling the ion exchange, the system 120 can encode information in the ionic exchange process. Thus, the system 120 uses ionic emission to encode information in the ionic exchange.

The control device 128 can vary the duration of a fixed ionic exchange rate or current flow magnitude while keeping the rate or magnitude near constant, similar to when the frequency is modulated and the amplitude is constant. Also, the control device 128 can vary the level of the ionic exchange rate or the magnitude of the current flow while keeping the duration near constant. Thus, using various combinations of changes in duration and altering the rate or magnitude, the control device 128 encodes information in the current flow or the ionic exchange. For example, the control device 128 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 120 may comprise electronic components as part of the control device 128. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 120 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 120 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Referring now back to FIG. 1, the mobile computer 50 is in communication with the data center 80. The data center 80 includes a database 82 and processing system 84.

Information associated with all patients, including identity and medication types and doses, are stored in the database 82. The processing system 84 receives information from the mobile computer 50 and accesses the information in the database 82 of the data center 80 to provide information to the care provider through the mobile computer 50. The mobile computer 50 can communicate information including a photo of the patient for identification, the type of medication available to the care provider, as well as confirmation of the type and dose of medication that the care provider selects and delivers to the patient 60. The mobile computer 50 can communicate with the data center 80 using any mode and frequency of communication that is available in at the site, such as wireless, G2, G3, real-time, periodically based on predetermined time delays, as well as store and forward at later time.

FIG. 1 illustrates one aspect of the mobile computer 50. In various aspects, the mobile computer 50 may comprise or be implemented by a wireless device.

The mobile computer 50 generally may comprise various physical or logical elements implemented as hardware, software, or any combination thereof, as desired for a given set of design parameters or performance constraints. In various aspects, the physical or logical elements may be connected by one or more communications media. For example, communication media may comprise wired communication media, wireless communication media, or a combination of both, as desired for a given implementation.

As shown, the mobile computer 50 may comprise a display 58. The display 58 may be implemented using any type of visual interface such as a liquid crystal display (LCD).

As shown, the mobile computer 50 may comprise a memory 102. In various aspects, the memory 102 may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

The mobile computer 50 may comprise a processor 100 such as a central processing unit (CPU). In various aspects, the processor 100 may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor 510 also may be implemented by a controller, a microcontroller, an application specific integrated circuit (ASIC), a field programmable gate array (FPGA), a programmable logic device (PLD), and so forth.

In various aspects, the processor 100 may be arranged to run an operating system (OS) and various mobile applications. Examples of an OS include, for example, operating systems generally known under the trade name of Microsoft Windows OS, and any other proprietary or open source OS. Examples of mobile applications include, for example, a telephone application, a camera (e.g., digital camera, video camera) application, a browser application, a multimedia player application, a gaming application, a messaging application (e.g., e-mail, short message, multimedia), a viewer application, and so forth.

In various aspects, the processor 100 may be arranged to receive information through a communications interface 104. The communications interface 104 may comprises any suitable hardware, software, or combination of hardware and software that is capable of coupling the mobile computer 50 to one or more networks and/or devices, such as the pill 20, the tag 22, the device 40, interrogation unit 46, the patient identity confirmation device 70, the tag 32, the sleeve 34, and/or the data center 80, among other devices. The communications interface 104 may be arranged to operate with any suitable technique for controlling information signals using a desired set of communications protocols, services or operating procedures. The communications interface 104 may include the appropriate physical connectors to connect with a corresponding communications medium, whether wired or wireless.

Vehicles of communication include a network. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

Accordingly, in various aspects, the communications interface 104 may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the mobile computer 50 may include a wireless interface comprising one or more antennas, transmitters, receivers, transceivers, amplifiers, filters, control logic, and so forth.

In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

In various implementations, the described aspects may comprise part of a cellular communication system. Examples of cellular communication systems may include CDMA cellular radiotelephone communication systems, GSM cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) systems such as WCDMA, CDMA-2000, UMTS cellular radiotelephone systems compliant with the Third-Generation Partnership Project (3GPP), and so forth.

In various aspects, the mobile computer 50 includes the functionality to wirelessly receive and/or wirelessly transmit data, e.g., physiologic data.

Further, in various aspects, the mobile computer 50 may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

The mobile computer 50 may be implemented as a mobile telephone. For example, the mobile computer 50 may be implemented as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In addition to the standard voice function of a telephone, various aspects of mobile telephones may support many additional services and accessories such as short message service (SMS) for text messaging, email, packet switching for access to the Internet, java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth.

It is to be understood that this invention is not limited to particular embodiments or aspects described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A computer system comprising:
an interrogation device operative to read a unique identity from a tag comprising circuitry, the tag secured to a pill of a medication;
wherein the pill is configured to transmit a signal upon being ingested by a patient and comprises:
a first material;
a second material insulated from the first material; and
a control circuit electrically coupled to each of the first material and the second material;
wherein the first material and the second material are configured to generate a voltage potential difference as a result of being in contact with a conducting liquid;
wherein the control circuit is configured to be activated by the voltage potential difference and configured to alter a conductance between the first material and the second material to generate the signal;
a patient interface device configured to detect biometric information identifying the patient via physical contact therewith; and a processor operative to:
receive, from the interrogation device, the unique identity of the tag, wherein the unique identity is associated with at least one of an amount of the medication and a type of the medication;
receive, from the patient interface device, the biometric information;
query a database to confirm that the biometric information identifying the patient is associated with the amount of the medication and the type of the medication; and
record administration of the medication upon detection of the signal.

2. The computer system of claim 1, wherein the processor is operative to receive medical information regarding a correct amount of the medication and a correct type of medication for the patient.

3. The computer system of claim 1, wherein the processor is operative to communicate with a datacenter to at least one of retrieve medical information about the patient or provide information related to the medication to be administered to the patient.

4. The computer system of claim 3, wherein the processor is operative to:
communicate with at least one of a database or a processing system at the datacenter;
transmit information to the processing system; and
receive information from the processing system, wherein the processing system is operative to access the information in the database of the datacenter and provide the information to the patient through a computer.

5. The computer system of claim 1, wherein the processor is operative to validate at least one of a correct type of the medication and a correct amount of the medication selected by a care provider prior to dispensing the medication to the patient.

6. The computer system of claim 1, wherein the processor is operative to:
communicate with a memory of the interrogation device; and
receive the unique identity of the tag stored in the memory of the interrogation device.

7. The computer system of claim 1, wherein the processor is operative to identify the patient based on the biometric information.

8. The computer system of claim 1, wherein the processor is operative to receive an image of the patient captured by a camera on the patient interface device.

9. The computer system of claim 1, further comprising a display configured to provide patient information associated with the patient, wherein the patient information comprises at least one of an image of the patient, a medical history of the patient, or a next type and dose of medication to deliver to the patient.

10. A computer-implemented method comprising:
receiving, by a processor, a unique identity from a tag comprising circuitry secured to a pill of a medication;
wherein the unique identity is associated with at least one of an amount of the medication and a type of the medication;
wherein the pill comprises:
a first material;
a second material insulated from the first material; and
a control circuit electrically coupled to each of the first material and the second material;
wherein the first material and the second material are configured to generate a voltage potential difference as a result of being in contact with a conducting liquid; and
wherein the control circuit is configured to be activated by the voltage potential difference and configured to alter a conductance between the first material and the second material to generate the signal;
receiving, by the processor, biometric information identifying a patient via physical contact with a patient interface device;
receiving the signal transmitted by the pill upon the pill being ingested by a patient;
querying a database to confirm that the biometric information identifying the patient is associated with the amount of the medication and the type of the medication; and
recording administration of the medication upon detection of the signal.

11. The computer-implemented method of claim 10, further comprising at least one of:
retrieving, by the processor, medical information about the patient from a datacenter database; and
providing, by the processor, information related to the medication to be administered to the patient.

12. The computer-implemented method of claim 11, further comprising:
transmitting, by the processor, information to a processing system; and
receiving, by the processor, information from the processing system, wherein the processing system is operative to access the information in the datacenter database and provide the information to the patient through a computer.

13. The computer-implemented method of claim 10, further comprising:
validating, by the processor, at least one of a correct type of the medication and a correct amount of the medication selected by a care provider prior to dispensing the medication to the patient.

14. The computer-implemented method of claim 10, wherein the unique identity includes an origin of the medication.

15. The computer-implemented method of claim 10, further comprising:
communicating, by the processor, with a memory of an interrogation unit, the interrogation unit configured to receive the unique identity of the tag; and
receiving, by the processor, the unique identity of the tag stored in the memory of the interrogation unit.

16. The computer-implemented method of claim 10, wherein the processor is operative to identify the patient based on the biometric information.

17. The computer-implemented method of claim 10, further comprising:
receiving, by the processor, an image of the patient captured by a camera on the patient interface device.

18. The computer-implemented method of claim 10, further comprising:
displaying, on a display coupled to the processor, patient information associated with the patient, wherein the patient information comprises at least one of an image of the patient, medical history of the patient, or a next type and dose of medication to deliver to the patient.

19. A computer system comprising:

an interrogation device operative to read a unique identity from a tag comprising circuitry, the tag secured to a syringe containing a medication;

wherein the syringe is configured to transmit a signal upon contacting a patient and comprises electrical contacts configured to cause a circuit to transmit a signal upon the electrical contacts contacting the patient;

a patient interface device configured to detect biometric information identifying the patient via physical contact therewith; and a processor operative to:
- receive, from the interrogation device, the unique identity of the tag, wherein the unique identity is associated with at least one of an amount of the medication and a type of the medication;
- receive, from the patient interface device, the biometric information;
- query a database to confirm that the biometric information identifying the patient is associated with the amount of the medication and the type of the medication; and
- record administration of the medication upon detection of the signal.

20. The computer system of claim 19, wherein the syringe comprises a needle and wherein the needle comprises at least one contact point coupled to the tag.

21. A computer-implemented method comprising:

receiving, by a processor, a unique identity from a tag comprising circuitry secured to a syringe of a medication;

wherein the unique identity is associated with at least one of an amount of the medication and a type of the medication;

wherein the syringe comprises electrical contacts configured to cause a circuit to transmit a signal upon the electrical contacts contacting a patient:

receiving, by the processor, biometric information identifying a patient via physical contact with a patient interface device;

receiving the signal transmitted by the syringe upon the syringe contacting the patient;

querying a database to confirm that the biometric information identifying the patient is associated with the amount of the medication and the type of the medication; and recording administration of the medication upon detection of the signal.

22. The computer-implemented method of claim 21, wherein the syringe comprises a safety component which is activated upon exposure to air.

23. The computer-implemented method of claim 21, wherein the syringe comprises a needle and the needle comprises at least one contact point coupled to the tag.

* * * * *

UNITED STATES PATENT AND TRADEMARK OFFICE
CERTIFICATE OF CORRECTION

| | | |
|---|---|---|
| PATENT NO. | : 10,529,044 B2 | Page 1 of 1 |
| APPLICATION NO. | : 13/698953 | |
| DATED | : January 7, 2020 | |
| INVENTOR(S) | : Thompson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 197 days.

Signed and Sealed this
Seventh Day of February, 2023

Katherine Kelly Vidal
*Director of the United States Patent and Trademark Office*